US005863791A

United States Patent [19]

Baldszun et al.

[11] Patent Number: 5,863,791

[45] Date of Patent: Jan. 26, 1999

[54] COVER RECEPTACLE ASSEMBLY

[75] Inventors: Karl Baldszun, Schenefeld; Hero Gerken, Hamburg, both of Germany

[73] Assignee: Eppendorf-Netheler-Hinz GmbH, Hamburg, Germany

[21] Appl. No.: 947,968

[22] Filed: Oct. 8, 1997

[30] Foreign Application Priority Data

Jul. 11, 1996 [DE] Germany ........................ 196 45 892.7

[51] Int. Cl.[6] ...................................................... C12M 3/00

[52] U.S. Cl. .................................... 435/288.1; 435/304.1; 422/102; 436/810; 220/335; 220/336; 220/338; 220/339

[58] Field of Search ............................ 422/102; 436/810; 435/288.1, 304.1; 220/335, 336, 338, 339

[56] References Cited

U.S. PATENT DOCUMENTS

| | | | |
|---|---|---|---|
| 4,158,902 | 6/1979 | Chernack et al. | 16/150 |
| 4,386,714 | 6/1983 | Roberto et al. | 220/339 |
| 4,487,324 | 12/1984 | Ostrowsky | 215/253 |
| 4,713,219 | 12/1987 | Gerken et al. | 422/102 |
| 5,145,646 | 9/1992 | Tyranski | 422/102 |
| 5,683,659 | 11/1997 | Hovatter | 422/105 |

FOREIGN PATENT DOCUMENTS

| | | |
|---|---|---|
| 1010761 | 11/1957 | Germany . |
| 7915283 | 5/1979 | Germany . |
| 8337595 | 3/1984 | Germany . |
| WO9511083 | 4/1995 | WIPO . |

*Primary Examiner*—David A. Redding

*Attorney, Agent, or Firm*—Anderson, Kill & Olick, P.C.

[57] ABSTRACT

A cover receptacle assembly of plastics for use in laboratories, in particular for the polymerase chain reaction technique, comprising a tubular receptacle having a receptacle botton at one end and a receptacle opening at an opposite end, a cover for sealingly closing said receptacle opening, strap hinge means integrally and pivotally connecting said receptacle and cover with each other, and holding means for holding said cover in an intermediate position between an initial position wherein said cover is pivoted away from said receptacle opening for 180° and a closing position wherein said cover closes said receptacle opening.

13 Claims, 6 Drawing Sheets

COVER RECEPTACLE ASSEMBLY

BACKGROUND OF THE INVENTION

1. Field of the Invention

This invention relates to a cover receptacle assembly of plastics for use in laboratories, in particular for the polymerase chain reaction (PCR) technique. The cover receptacle assembly is intended for small probes and may have a capacity of about 0.2 to 0.5 ml.

2. Description of Related Art

Cover receptacle assemblies of the prior art comprise a tubular receptacle and a cover connected thereto adjacent the receptacle opening by means of a flap. In a reaction receptacle of plastics as disclosed in European patent 0 149 797 B1 the flap comprising strap hinge means is integrally connected both to the receptacle and the cover. For facilitating injection molding of such assemblies the structure thereof is such that the cover normally assumes a position wherein it is laterally pivoted away from its closing position for 180° and the strap hinge means extends parallel to the receptacle opening. Due to the resilience of the strap hinge means the cover remains in such an initial position or returns thereto unless it is being held in its closing position. As a result the cover receptacle assembly when being in its open condition requires a lot of space.

Quite often a great number of cover receptacle assemblies are inserted in holders to allow for the simultaneous handling of various probes, which holders have apertures arranged in parallel rows to receive the cover receptacle assemblies. Such holders may belong for example to heating or mixing devices. Furthermore, it has become known to interconnect a plurality of cover receptacle assemblies by strip portions so as to form receptacle strip assemblies in order to allow for simultaneous handling thereof even when they are not positioned in a common holder. One field of use is the polymerase chain reaction (PCR) technique wherein a temperature program is being executed in a heating device. When therein a temperature of more than 90° C. has been reached, DNA is being separated into its two rods. At temperatures of about 40° to 70° C. copies of the DNA are being made by use of a primer. The DNA is being multiplied in a plurality of heating and cooling cycles.

When the probes are being handled simultaneously, the substantial space requirement of the open cover receptacle assemblies is particularly disadvantageous. This is so because they must be filled and unfilled when they are positioned within the holder. If laterally projecting covers overlap adjacent receptacle openings, pipetting of the probes becomes difficult and the risk of contamination thereof is enhanced. When the receptacle rows are largely spaced from each other in order to avoid this, the holders and accordingly the heating and other auxiliary devices will become voluminous and expensive.

SUMMARY OF THE INVENTION

It is an object of the present invention to provide a cover receptacle assembly which avoids the above drawbacks. A further object is to provide cover receptacle assemblies which require less space when they are arranged in groups in parallel relationship to each other and when their covers are not in their closing position.

The present invention provides a cover receptacle assembly of plastics for use in laboratories, in particular for the polymerase chain reaction technique, comprising a tubular receptacle having a receptacle botton at one end and a receptacle opening at an opposite end, a cover for sealingly closing said receptacle opening, strap hinge means integrally and pivotally connecting said receptacle and cover with each other, and holding means for holding said cover in an intermediate position between an initial position wherein said cover is pivoted away from said receptacle opening for 180° and a closing position wherein said cover closes said receptacle opening.

The holding means allows for the cover to be pivoted into a stable intermediary position so that a plurality of cover receptacle assemblies may be disposed in groups adjacent each other in a space-saving manner, with the receptacle openings not being overlapped by laterally projecting covers of adjacent assemblies and the receptacle openings being freely accessible for the pipetting of probes. Furthermore, the risk of contamination of the probes is drastically reduced thereby. The invention facilitates handling of the probes, improves quality of work and reduces apparatus expenditure. Nevertheless, the cover receptacle assemblies still may be injection molded with the cover being pivoted away from the receptacle opening for 180°.

Preferably, the holding means comprise a locking nose member and a locking edge member, with one of said members being integral with the cover and the other being integral with the receptacle. Said members snappingly engage each other when the cover is pivoted from its initial position towards the intermediate position due to a resilient deflection of at least one of said members of said holding means and/or said strap hinge means. When the locking nose member and the locking edge member snappingly engage each other, they hold the cover in its stable intermediate position (preferably spaced from its closing position for about 75° to 90°). The resilient forces exerted by the flexible strape hinge means may urge the cover into its stable intermediate position wherein the locking nose member and the locking edge member engage each other so as to prevent the cover from pivoting back into its initial position (which is spaced from the closing position for about 180°). However, further pivoting of the cover into its closing position is still possible.

For injection molding purposes it is preferred that said locking nose member extends substantially perpendicularly to a plane containing said receptacle opening and said locking edge member extends substantially parallel to said plane.

In a preferred embodiment said locking nose member includes on opposite sides locking projections and is arranged so as to be aligned with a gap between a pair of fork tines comprising locking edges, with said gap being parallel to said strap hinge means, and said locking nose member is arranged to have locking projections resiliently spread said fork tines until their locking projections engage behind said locking edges of said fork tines when said cover is being pivoted towards said intermediate position. The cover is now in its stable intermediate position into which the holding means are urged by the resilient forces of the strap hinge means. When the cover is pivoted further towards its closing position, the locking nose member and the fork tines do not interfere with each other. Furthermore, the locking nose member may have its locking projections spaced from the fork tines when the cover is in the initial position; this may simplify manufacture and furthermore may facilitate return movement of the cover towards its initial position during which the locking nose member and the fork tines slide along each other until they will become free.

Preferably, a plurality of cover receptacle assemblies are integrally interconnected by strip portions adjacent their receptacle openings so as to form receptacle strip assemblies. The interconnecting strip portions may extend under an angle of about 45° with respect to the strap hinge means of the cover receptacle assemblies in order to save even more space.

BRIEF DESCRIPTION OF THE DRAWINGS

Preferred embodiments of the invention will be described in more detail in the following with reference to the accompanying drawings wherein.

DESCRIPTION OF PREFERRED EMBODIMENTS

Figure 1:
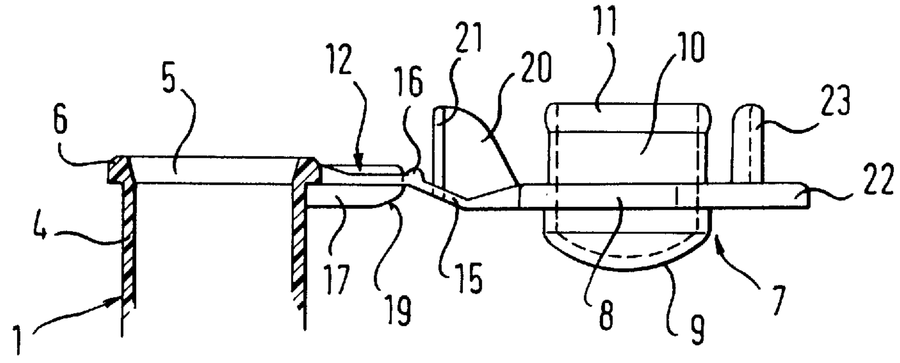
FIG. 1 shows the upper part of a first embodiment of a cover receptacle assembly in a side elevation (scale 4:1), with the cover being in its initial position.

In the following description corresponding elements of different embodiments have been designated by the same reference numerals.

The cover receptacle assembly of FIGS. 1 to 4 comprises a receptacle 1 having a cup-shaped bottom 2, an adjacent conical portion 3 and an adjacent cylindrical portion 4 which includes a receptacle opening 5 and a receptacle flange 6 extending thereabout.

Further the cover receptacle assembly comprises a cover 7 having a cover flange 8 which carries externally a convex cover cap 9 and internally an annular sealing collar 10 including an end-wise sealing bead 11.

The receptacle 1 and the cover 7 are connected to each other by a pair of parallel hinge straps 12 which extend from the receptacle flange 6 to the cover flange 8. The hinge straps 12 have side portions 13 adjacent the receptacle flange 6 and side portions 14 adjacent the cover flange 8, which side portions 13,14 are practically unflexible. Therebetween they have flexible central portions 15. Projections 16 are provided upon the central portions 15, with the hinge straps 12 being foldable about the projections 16.

Parallel fork tines 17 extend from the receptacle flange 6 and, respectively, the cylindrical portion 4 between the hinge straps 12, a gap 18 parallel to the hinge straps 12 being provided between the fork tines 17. The fork tines 17 extend substantially to the projections 16. They are provided at their lower side with locking edges 19 which are somewhat tapered towards the free ends of the fork tines 17.

A locking nose 20 is aligned to the gap 18 and has its end connected to the cover flange 8. The locking nose 20 is spaced from the fork tines 17 for somewhat more than the width of the projections 16 when the cover 7 is in its initial position (see FIG. 2). Its width is somewhat less than the width of the gap 18. However, it is provided on opposite sides with locking projections 21 such that its width thereat somewhat exeeds the width of the gap 18. The locking nose 20 has its locking projections 21 extend perpendicularly to the cover flange 8.

Finally the cover flange 8 carries at its side opposite the hinge straps 12 a projecting flap portion 22. A cylindrical wall portion 23 is disposed thereon so as to extend from the cover flange 8 approximately as far as the sealing collar 10.

Figure 2:
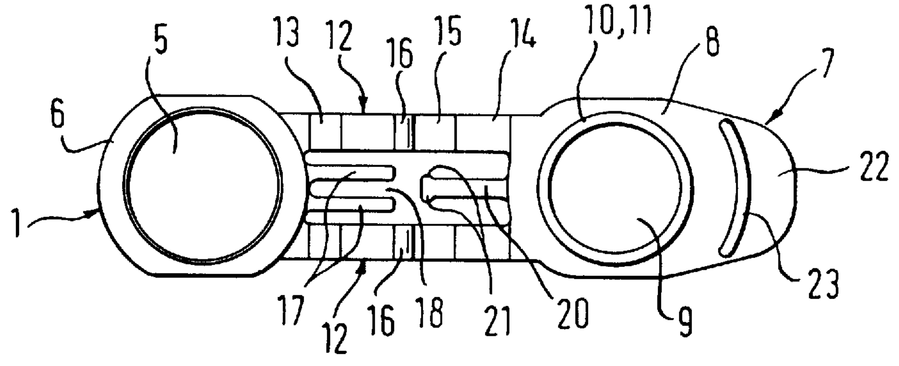
FIG. 2 is an elevation of the cover receptacle assembly in FIG. 1.

The total cover receptacle assembly is integrally injection molded from a resilient plastics material such as polypropylene. It is removed from the injection die in a shape as shown in FIGS. 1 and 2, in which it can be easily removed. Due to internal material forces the cover 7 retains its initial position in which it is pivoted away from the receptacle opening 5 for 180° unless it will be deflected by external forces.

Figure 3:
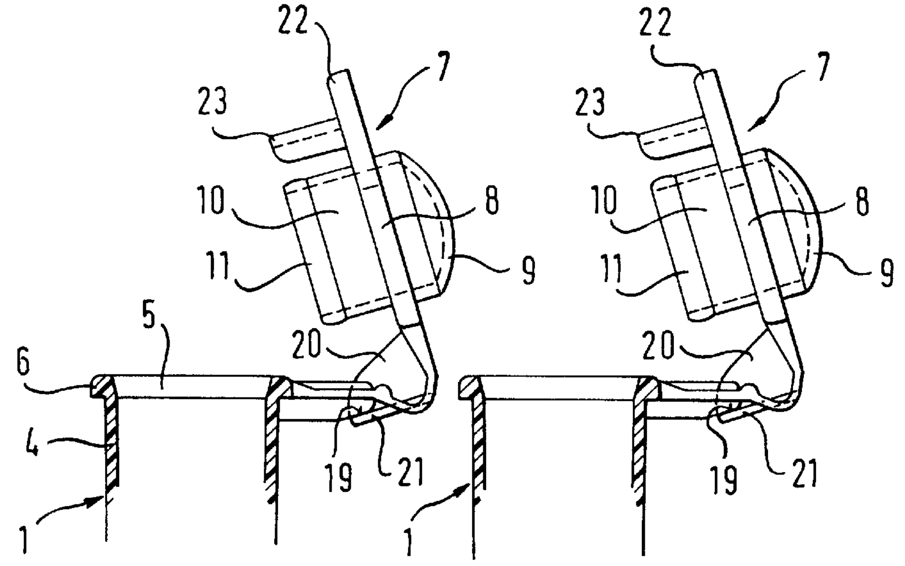
FIG. 3 is a side elevation of a pair of cover receptacle assemblies in parallel adjacent relationship, with the covers thereof being in their stable intermediate positions.

When the cover is pivoted towards the receptacle opening 5, the nose 20 enters the gap 18 between the fork tines 17 and has its locking projections 21 spread them slightly. As soon as the locking projections 21 will be below the locking edges 19 of the fork tines 17, the latter slightly snap in. When the cover 7 will then be released, the resilient forces of the hinge straps 15 intend to pivot the cover 7 back towards its initial position. However, the locking edges 21 are retained by the locking edges 19, and the cover 7 is retained in its intermediary position. This is shown in FIG. 3. Due to the taper of the locking edges 19 the angle between the intermediate position of the cover 7 and the closing position of the cover 7 at the opening 5 is about 75°. FIG. 3 shows that a pair of identical cover receptacle assemblies with the receptacle 1 being parallel to each other may be positioned closely adjacent to each other. Because the covers 7 have been pivoted somewhat across the receptacles 1, they do not interfere when a cover receptacle assembly is being moved vertically into an adjacent position.

Figure 4:
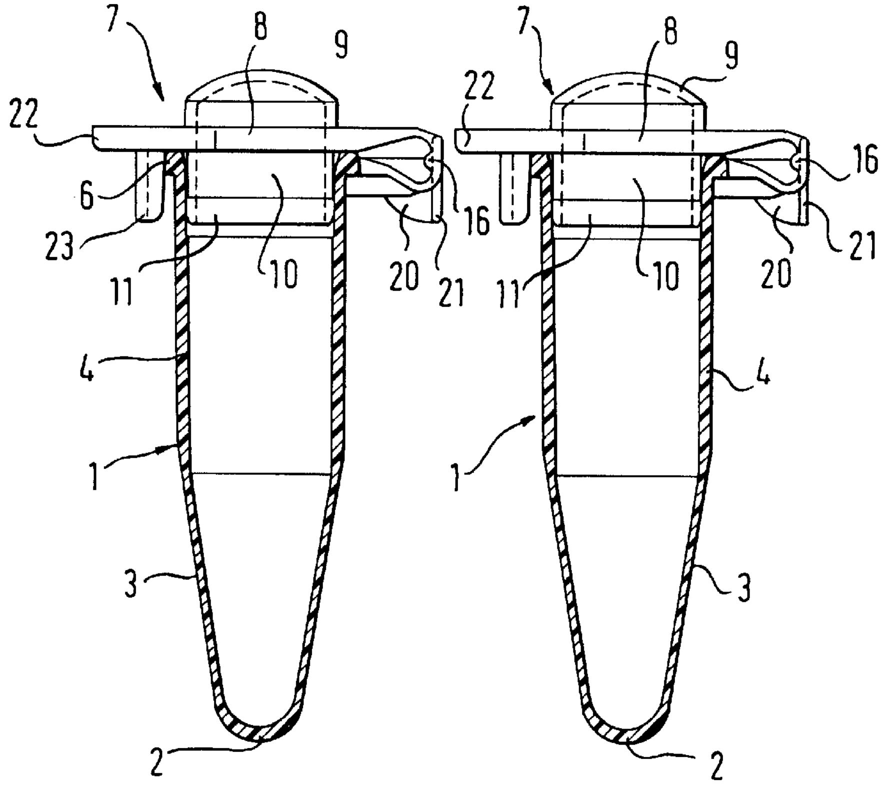
FIG. 4 is a side elevation of the pair of cover receptacle assemblies in FIG. 3, with the covers being in their closing positions.

When the covers 7 are pivoted from their stable intermediate positions into the closing positions at the receptacle openings 5, the locking projections 21 move away from the locking edges 19, and the locking noses 20 move through the gaps 18. The sealing collar 10 enters the receptacle opening 5 and has its sealing bead 11 pressed into the cylindrical portion 4 until the cover flange 8 will lie upon the receptacle flange 6. FIG. 4 shows a pair of adjacent cover receptacle assemblies in their closing positions wherein the covers 7 are sealed and retained by the sealing beads 11.

In order to re-open the cover the cover flange 8 can be raised by means of the flap portion 22 or the cylindrical wall portion 23. As a result the locking projections 21 will slide along the locking edges 19 outwards until they will slide off from the ends of the fork tines 17. This will be the case only when the cover 7 has reached almost its initial position shown in FIGS. 1 and 2. This will facilitate to reach again the stable intermediate position of FIG. 3 after the cover 7 will have been moved in its opening position.

Pivoting of the cover from its initial position into its stable intermediate position and into the closing position and from the latter back into the stable intermediate position or into the initial position may be performed automatically and simultaneously for a group of cover receptacle assemblies.

Figure 5:
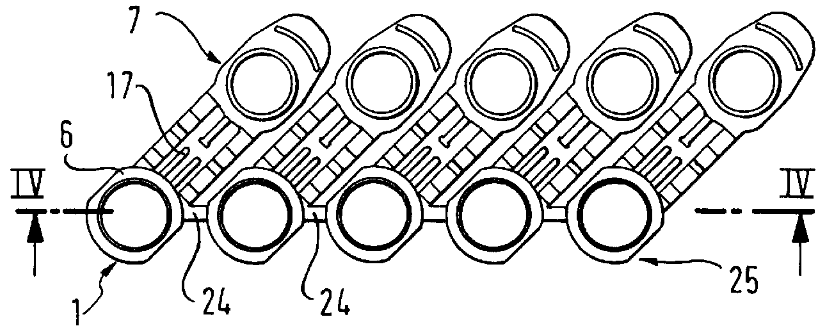
FIG. 5 is an elevation of a part of a receptacle strip assembly comprised of cover receptacle assemblies as shown in the preceding Figures (scale 2:1)
Figure 6:
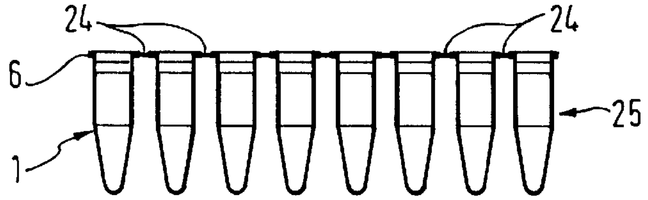
FIG. 6 is a cross-section along line VI—VI of the receptacle strip assembly in FIG. 5 (scale 1:1)

FIGS. 5 and 6 show a group of cover receptacle assemblies which are interconnected with each other by strip portions 24 between adjacent receptacle flanges 6 so as to form receptacle strip assemblies 25.

Figure 7:
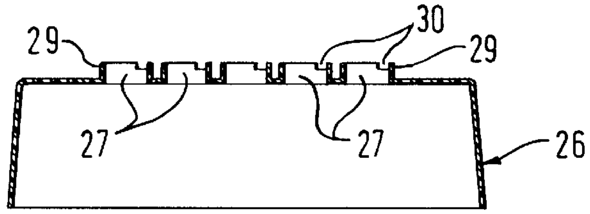
FIG. 7 is a cross-section of a holder for the receptacle strip assembly in FIGS. 5 and 6 (scale 1:1)
Figure 8:
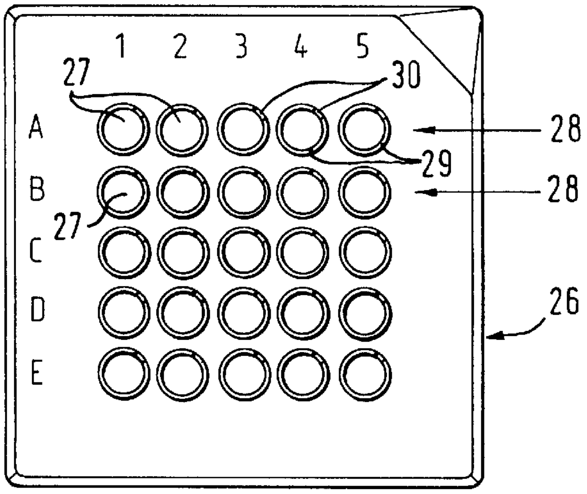
FIG. 8 is an elevation of the holder in FIG. 7.

As shown in FIGS. 7 and 8 a holder 26 has apertures 27 in parallel rows 28 for receptacle strip assemblies 25 including five cover receptacle assemblies. The apertures 27 are surrounded by upwardly extending support collars 29 having a small groove 30 for receiving and positioning of the fork tines 17.

Figure 9:
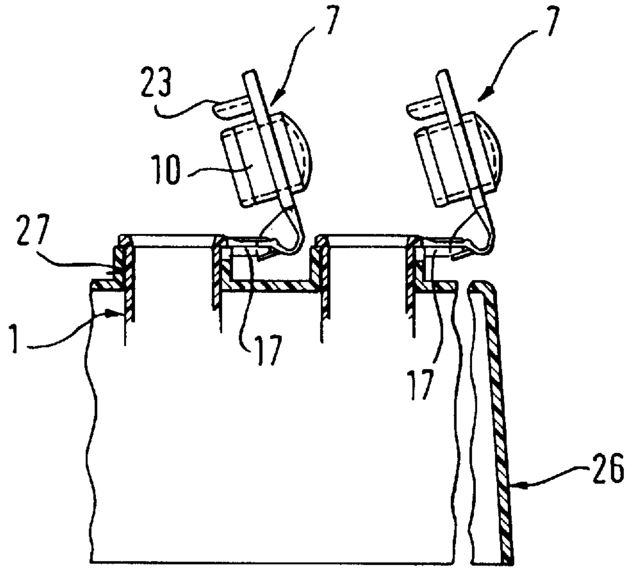
FIG. 9 is a partial cross-section of a holder in which parallel receptacle strip assemblies are inserted, with the covers being in their stable intermediate positions (scale 2:1)
Figure 10:
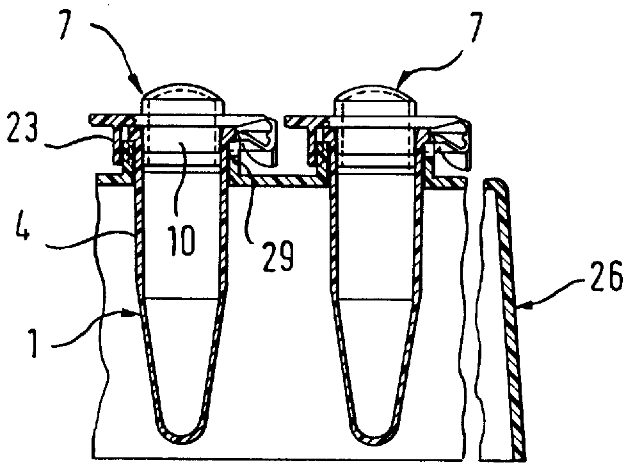
FIG. 10 is a partial cross-section of the holder in FIG. 9, with the covers being in their closing positions.

FIGS. 9 and 10 show the holder 26, the apertures 27 of which receive cover receptacle assemblies with opened covers 7 (FIG. 9) and with closed covers 7 (FIG. 10). When the cover 7 is in its closed position the support collar 29 is clamped between the cylindrical portion 4 of the receptacle 1 and the cylindrical wall portion 22 of the cover 7 whereby the cover receptacle assemblies are secured to the holder 26.

Figure 11:
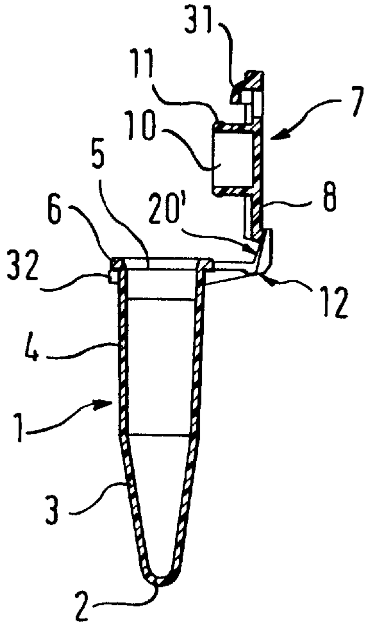
FIG. 11 is a longitudinal section of another embodiment of a cover receptacle assembly, with the cover being in its stable intermediate position (scale 2:1)
Figure 12:
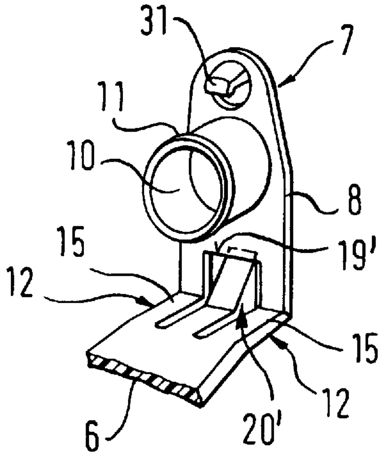
FIG. 12 is an enlarged perspective view of a cover for the cover receptacle assembly in FIG. 11.

In the embodiments of FIGS. 11 and 12 a locking nose 20' is laterally connected to the receptacle flange 6 and formed as a hook extending upwards from the plane of the receptacle flange 6. The locking nose 20 is disposed between flexible central portions 15 and a pair of parallel hinge straps 12 which are connected at one end to the receptacle flange 6 and at an opposite end to the cover flange 8. The cover flange 8 has a locking edge 19' extending between the hinge straps 12 perpendicularly to the pivot plane thereof.

The locking edge 19' will be urged across the locking nose 20' when the cover 7 is pivoted towards the opening 5 and will be spaced therefrom for 90°. The flexibility of the locking nose 20 or, respectively, of the hinge straps 5 will enable the locking edge 19' to be raised across the end of the locking nose 20'.

When the cover 7 will then be released, its locking edge 19' will be urged against the locking nose 20' due to the resilience of the central portions 15 such that it will remain in such stable intermediate position. The cover 7 will be readily pivoted further towards its closing position because the locking edge 19' will then be released from the locking nose 20'. When the cover 7 is in its closing position, its locking hook 31 will snap behind a locking cam 32 adjacent the receptacle opening 5 whereby the cover 7 will be secured in its closing position. However, the cover 7 can be unlocked and opened whereupon it may return into its stable intermediate position by itself. Furthermore, it may be urged back into its initial position, a taper of the locking nose 20' will help to raise the locking edge 19'.

Figure 13:
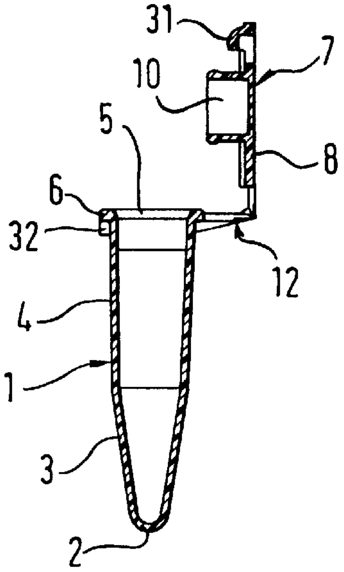
FIG. 13 is a longitudinal section of a further embodiment of a cover receptacle assembly, with the cover being in its stable intermediate position (scale 2:1)
Figure 14:
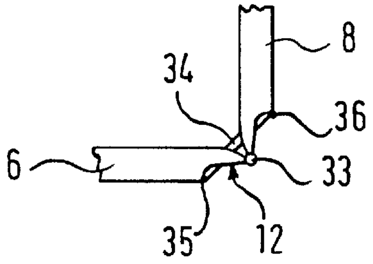
FIG. 14 is an enlarged side elevation of strap hinge means for the cover receptacle assembly in FIG. 13 with the cover being in its stable intermediate position.
Figure 15:
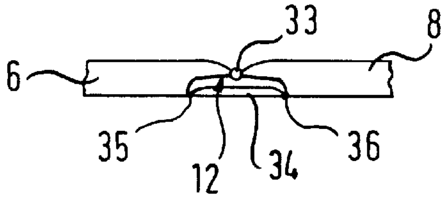
FIG. 15 is an enlarged partial side elevation of the strap hinge means of FIG. 14, with the cover being in its original position.

In the embodiment of FIGS. 13 to 15 a pair of parallel hinge straps 12 is also disposed between the receptacle flange 6 and the cover flange 8, with the flexibility of the hinge straps 12 being confined substantially to the limited area of its pivot axis 32. To this end they will rapidly decrease in thickness towards the pivot axis 33.

The receptacle flange 6 and the cover flange 8 are interconnected by a further hinge strap 34 which is disposed between the hinge straps 12. The further hinge strap 34 includes a hinge 35 at the receptacle flange 6 and a hinge 36 at the cover flange 8. However, the further hinge strap 34 is relatively thin also between the hinges 35 and 36 so that it can be stretched resiliently. When the cover receptacle assembly has been injection molded, the cover 7 again is pivoted away from the receptacle opening 5 for about 180°. When the cover is in this initial position, the further hinge strap 34 is not tensioned (FIG. 15). When the cover 7 is now pivoted about the pivot axis 33, the spacing between the hinges 35 and 36 will increase, and the further hinge strap 34 will be resiliently stretched slighter until it will be positioned along the pivot axis 33. When thereafter the cover 7 is pivoted further towards its closing position, the further hinge strap 34 will contract somewhat until it will have its original length. This will be the case when the cover 7 includes an angle of about 90° with the receptacle opening 5 (FIG. 14). When the cover 7 is in this stable intermediate position, it will be stabilized with respect to the receptacle 1 by the further hinge strap 34. When the cover 7 will be pivoted further towards its closing position, the further hinge strap 34 will be deflected outwards. When the cover 7 will be in its closing position, however, the locking hook 31 together with the locking cam 32 will prevent the cover 7 from moving in an opening direction. When the cover 7 will have been unlocked, it may be moved again into its stable intermediate position or into its initial position.

We claim:

1. A cover receptacle assembly of plastics for use in laboratories, in particular for the polymerase chain reaction technique, comprising:

a tubular receptacle (1) having a receptacle button (2) at one end and a receptacle opening (5) at an opposite end;

a cover (7) for sealingly closing said receptacle opening (5);

strap hinge means (12) integrally and pivotally connecting said receptacle (1) and cover (5) with each other, and holding means (20, 19; 34) for holding said cover (7) in an intermediate position between an initial position wherein said cover is pivoted away from said receptacle opening (5) for 180° and a closing position wherein said cover closes said receptacle opening (5), wherein said holding means comprises a locking nose member (2) and a locking edge member (19), one of said locking nose member (2)) and said locking edge member (19) being integral with said cover (7) and the other of said members being integral with said receptacle (1), said locking nose member (20) and said locking edge member (19) being arranged to snappingly engage each other when the cover (7) is moved from said initial position towards said intermediate position so as to prevent said cover (7) when it is in its intermediate position from pivoting back into said initial position and to allow for further pivoting of said cover (7) towards said closing position.

2. A cover receptacle assembly as defined in claim 1, wherein said locking nose member (20) extends substantially perpendicularly said locking edge member (13) extends substantially parallel to a plane containing said receptacle opening.

3. A cover receptacle assembly as defined in claim 1, wherein said locking nose member (20) includes on opposite sides locking projections (21) and is arranged so as to be aligned with a gap between a pair of fork tines (17) comprising locking edges (19), with said gap being parallel to said strap hinge means (12), and said locking nose member (20) is arranged to have locking projections (21) resiliently spread said fork tines (17) until their locking projections (21) engage behind said locking edges (19) of said fork tines (17) when said cover (7) is being pivoted towards said intermediate position.

4. A cover receptacle assembly as defined in claim 3, wherein the locking projections (21) of said locking nose member (20) are spaced from said fork tines (17) when said cover (7) is in said initial position.

5. A cover receptacle assembly as defined in claim 3, wherein said locking nose member (20) is integral with said cover (7) and said fork tines (17) are integral with said receptacle (1).

6. A cover receptacle assembly of plastics for use in laboratories, in particular for the polymerase chain reaction technique, comprising:

a tubular receptacle (1) having a receptacle button (2) at one end and a receptacle opening (5) at an opposite end;

a cover (7) for sealingly closing said receptacle opening (5);

strap hinge means (12) integrally and pivotally connecting said receptacle (1) and cover (5) with each other, and holding means (20, 19; 34) for holding said cover (7) in an intermediate position between an initial position wherein said cover is pivoted away from said receptacle opening (5) for 180° and a closing position wherein said cover closes said receptacle opening (5), wherein said strap hinge means comprises a pair of parallel hinge straps (12) and said holding means (20, 19; 34) is arranged between said hinge straps (12), and wherein said holding means comprises a resiliently deflectable locking hook member (20') extending between said hinge straps (12) substantially perpendicularly to a plane containing said receptacle (1) and a locking edge member (19') extending substantially perpendicularly to the pivot axis of said strap hinge means (12) in said plane.

7. A cover receptacle assembly as defined in claim 1, wherein said cover (7) has a sealing collar (10) adapted to engage into said receptacle opening (5) when said cover (7) is pivoted into said closing position.

8. A cover receptacle assembly as defined in claim 1, wherein said cover (7) includes a locking hook (31) and said receptacle (1) includes a locking cam (32) adjacent said receptacle opening (5), said locking hook (31) engaging behind said locking cam (32) when said cover is in said closing position.

9. A cover receptacle assembly as defined in claim 1, wherein said cover (7) includes a cylindrical wall portion (23) on a side diametrically opposite to said strap hinge means (12).

10. A cover receptacle assembly as defined in claim 1, wherein said locking nose member (20) and said locking edge member (19) are integral with flanges of said cover (7) and, respectively, said receptacle (1).

11. A cover receptacle assembly of plastics for use in laboratories, in particular for the polymerase chain reaction technique, comprising:

a tubular receptacle (1) having a receptacle button (2) at one end and a receptacle opening (5) at an opposite end;

a cover (7) for sealingly closing said receptacle opening (5);

strap hinge means (12) integrally and pivotally connecting said receptacle (1) and cover (5) with each other, and holding means (20, 19; 34) for holding said cover (7) in an intermediate position between an initial position wherein said cover is pivoted away from said receptacle opening (5) for 180° and a closing position wherein said cover closes said receptacle opening (5), wherein said strap hinge means comprises a pair of parallel hinge straps (12) and said holding means (20, 19; 34) is arranged between said hinge straps (12), and wherein said holding means comprises a further hinge strap (34) having one end pivotally connected to said cover (7) and having an opposite end pivotally connected to said receptacle (1), which hinge strap (34) is arranged so as to be untensioned when said cover is in any of said initial and intermediate positions and to be resiliently tensioned when said cover (7) is in other positions.

12. A receptacle strip assembly, comprising:

a plurality of cover receptacle assemblies of plastics for use in laboratories, each cover receptacle assembly having;

a tubular receptacle (1) having a receptacle button (2) at one end and a receptacle opening (5) at an opposite end;

a cover (7) for sealingly closing said receptacle opening (5);

strap hinge means (12) integrally and pivotally connecting said receptacle (1) and cover (5) with each other, and holding means (20, 19; 34) for holding said cover (7) in an intermediate position between an initial position wherein said cover is pivoted away from said receptacle opening (5) for 180° and a closing position wherein said cover closes said receptacle opening (5); and a plurality of strip portions (24) for integrally connecting the plurality of cover receptacle assemblies adjacent the receptacle openings (5) of said plurality of cover receptacle assemblies, wherein said strip portions (24) interconnecting said plurality of cover receptacle assemblies are inclined to the strap hinge means (12) of said plurality of cover receptacle assemblies under an angle of about 45°.

13. A cover receptacle assembly as defined in claim 11, wherein said further hinge strap (34) is positioned between said pair of first mentioned parallel hinge straps (12).

* * * * *